(12) United States Patent
Haghighi-Mood et al.

(10) Patent No.: US 7,197,358 B2
(45) Date of Patent: Mar. 27, 2007

(54) IDENTIFYING INFANTS AT RISK FOR SUDDEN INFANT DEATH SYNDROME

(75) Inventors: Ali Haghighi-Mood, Andover, MA (US); Richard J. Cohen, Chestnut Hill, MA (US)

(73) Assignee: Cambridge Heart, Inc., Bedford, MA (US)

( * ) Notice: Subject to any disclaimer, the term of this patent is extended or adjusted under 35 U.S.C. 154(b) by 494 days.

(21) Appl. No.: 10/173,307

(22) Filed: Jun. 18, 2002

(65) Prior Publication Data

US 2003/0233050 A1   Dec. 18, 2003

(51) Int. Cl.
*A61B 5/0444* (2006.01)

(52) U.S. Cl. ............................... 600/517; 600/508
(58) Field of Classification Search ......... 600/508–528
See application file for complete search history.

(56) References Cited

U.S. PATENT DOCUMENTS

| | | | |
|---|---|---|---|
| 4,802,491 A * | 2/1989 | Cohen et al. ............... | 600/515 |
| 5,265,617 A | 11/1993 | Verrier et al. | |
| 5,348,020 A * | 9/1994 | Hutson ........................ | 600/509 |
| 5,437,285 A | 8/1995 | Verrier et al. | |
| 5,570,696 A | 11/1996 | Arnold et al. | |
| 5,704,365 A | 1/1998 | Albrecht et al. | |
| 5,713,367 A | 2/1998 | Arnold et al. | |
| 5,724,984 A * | 3/1998 | Arnold et al. .............. | 600/372 |
| 5,791,944 A | 8/1998 | Grant et al. | |
| 5,827,195 A | 10/1998 | Lander | |
| 5,891,045 A | 4/1999 | Albrecht et al. | |
| 5,891,047 A | 4/1999 | Lander et al. | |
| 5,902,250 A * | 5/1999 | Verrier et al. ............... | 600/515 |
| 5,908,393 A | 6/1999 | Albrecht et al. | |
| 5,935,082 A | 8/1999 | Albrecht et al. | |
| 6,047,206 A | 4/2000 | Albrecht et al. | |
| 6,253,107 B1 | 6/2001 | Albrecht et al. | |
| 6,453,191 B2 * | 9/2002 | Krishnamachari .......... | 600/515 |
| 6,735,466 B1 * | 5/2004 | Haghighi-Mood .......... | 600/515 |
| 6,856,831 B2 * | 2/2005 | Griffin et al. ............... | 600/515 |

FOREIGN PATENT DOCUMENTS

| | | |
|---|---|---|
| CA | 1310071 | 11/1992 |
| DE | 3788251 | 3/1994 |

(Continued)

OTHER PUBLICATIONS

Sadeh et al.; *QT Interval in Sudden Infant Death—Altered Cardiac Repolarization in Some Victims of Sudden Infant Death Syndrome*; The New England Journal of Medicine; vol. 317, No. 24; pp. 1501-1505; Dec. 10,1987.

(Continued)

*Primary Examiner*—George R. Evanisko
*Assistant Examiner*—Terri Lynn Smith
(74) *Attorney, Agent, or Firm*—Fish & Richardson P.C.

(57) ABSTRACT

Identifying infants at risk for SIDS includes applying electrodes to an infant, receiving electrical signals from the electrodes, analyzing the received electrical signals to measure alternans of a heart of the infant, and identifying whether the infant is at risk for SIDS. A system for identifying infants at risk for SIDS includes an input unit configured to receive electrical signals from electrodes applied to an infant, a processor connected to the input unit and configured to process the received electrical signals to measure alternans of a heart of the infant, and a comparator configured to compare the measured alternans with alternans in a population of infants.

36 Claims, 8 Drawing Sheets

FOREIGN PATENT DOCUMENTS

| | | |
|---|---|---|
| EP | 0255348 | 2/1988 |
| EP | 0746229 | 12/1996 |
| JP | 9508293 | 8/1997 |
| WO | 9520351 | 8/1995 |
| WO | 9614796 | 5/1996 |

OTHER PUBLICATIONS

Schwartz et al.; *Prolongation of the QT Interval and the Sudden Infant Death Syndrome*; The New England Journal of Medicine; vol. 338(24); pp. 1709-1714; Jun. 11, 1998.

S. Lawrence Marple, Jr.; "Computing the Discrete-Time 'Analytic' Signal Via FFT"; *Asilomar Conference on Signals, Systems and Computers*, US, Los Alamitos, CA IEEE; Nov. 2, 1997; pp. 1322-1325.

O. Fokapu et al.; "A New Approach For P Wave Detection Using Analytic Signal"; *Proceedings of the Annual International Conference of Engineering in Medicine and Biology Society*, US, New York, IEEE vol. Conf. 15; Oct. 28, 1993; pp. 400-401.

Mustafa A. Murda'H et al.; "Repolarization Alternans: Techniques, Mechanisms, and Cardiac Vulnerability"; *PACE—Pacing and Clinical Electrophysiology*, Futura Publishing Company, Inc., US; vol. 20, No. 10, Part 02; Oct. 1, 1997; pp. 2641-2657.

Smith JM, Clancy EA, Valeria CR et al.; *Electrical alternans and cardiac electrical instability*; Circulation 1988; 77: 110-121.

Adam Dr., Smith JM, Akselrod S et al., *Fluctuations in T-Wave morpnology and susceptibility to ventricular fibrillation*, Journal of Electrocardiology (London), 1984; 17:209-218.

Patent Cooperation Treaty International Search Report dated Dec. 18, 2000; Application No. PCT/US00/26822 filed Sep. 9, 2000.

* cited by examiner

Fig. 12A Analytical method

Fig. 12B Spectral method

FIG. 13

IDENTIFYING INFANTS AT RISK FOR SUDDEN INFANT DEATH SYNDROME

TECHNICAL FIELD

This disclosure is directed to the identification of infants at risk for the Sudden Infant Death Syndrome.

BACKGROUND

The Sudden Infant Death Syndrome (SIDS) is a disorder in which infants suddenly die, usually during sleep. For every one thousand infants, between approximately one and two die of SIDS, making SIDS the leading cause of death after the neonatal period in the first year of life. SIDS is thus an enormous human tragedy that has devastating consequences for the affected infants and their families.

SUMMARY

Improved identification of infants at risk for SIDS is provided by measurement of alternans, for example, T-wave alternans, of an infant heart. Alternans is a subtle beat-to-beat change in the repeating pattern of an infant's or other patient's electrocardiogram (ECG) waveform. Alternans results in an ABABAB . . . pattern of variation of waveform shape between successive beats in an ECG waveform. The level of variation is indicative of the likelihood that an infant is at risk for SIDS.

A method for identifying infants at risk for Sudden Infant Death Syndrome includes applying electrodes to an infant, receiving electrical signals from the electrodes, analyzing the received electrical signals to measure alternans of a heart of the infant, and identifying whether the infant is at risk for SIDS.

In another aspect, another method for identifying infants at risk for Sudden Infant Death Syndrome includes applying electrodes to an infant patient, receiving electrical signals from the electrodes, analyzing the received electrical signals to measure alternans of a heart of the infant, and comparing the measured alternans with alternans in a population of infants.

These methods may include one or more of the following features. For example, the received electrical signals may be analyzed to measure T-wave alternans, and the measured T-wave alternans may be compared with T-wave alternans in a population of infants. The method may also include elevating a heart rate of the infant.

Elevating the heart rate of the infant may include stressing the infant. The method may also include analyzing the received electrical signals to measure a QT interval of the heart of the infant. The method may also include comparing the measured QT interval with QT intervals in a population of infants. The received electrical signals may include electrocardiogram signals. Analyzing the received electrical signals may include sampling the processed signal at a frequency less than or equal to twice a frequency corresponding to alternans.

Analyzing the received electrical signals may include using a spectral approach to measure alternans. Using a spectral approach to measure alternans may include digitizing the waveform at a plurality of sample points for each cycle, and constructing two-dimensional sample point matrices, having rows and columns, from the digitized waveform. Using a spectral approach to measure alternans may also include analyzing variability in each column of the sample point matrices to form an index correlating with the physiologic stability. Using a spectral approach to measure alternans may also include computing the alternating energy at each of the sample points for the series of beats, and summing the alternating energy over the entire set of sample points to generate a total alternating energy.

Analyzing the received electrical signals may include using an analytical approach to measure alternans. Using the analytical approach may include processing the received electrical signals to create a processed signal having an asymmetric spectrum, and processing the processed signal to measure alternans in the received electrical signals. Processing the received electrical signals to create a processed signal may include creating the processed signal as an analytical signal. Creating the processed signal as an analytical signal may include generating a frequency domain representation of the received electrical signals, modifying the frequency domain representation to remove components corresponding to negative frequencies, and generating the analytical signal as a time domain representation of the modified frequency domain representation. Processing the processed signal may include processing samples of the processed signal spaced by intervals greater than or equal to half the period of alternans. Processing the received electrical signals may include creating an approximation of an analytical signal version of the received electrical signals. Processing the processed signal may include sampling the processed signal at a frequency less than or equal to twice a frequency corresponding to alternans.

A system for the identification of infants at risk for Sudden Infant Death Syndrome includes an input unit configured to receive electrical signals from electrodes applied to an infant, a processor connected to the input unit and configured to process the received electrical signals to measure alternans of a heart of the infant, and a comparator configured to compare the measured alternans with alternans in a population of infants This system may include one or more of the following features. For example, the processor may be configured to process the received electrical signals to measure T-wave alternans of the heart of the infant, and the comparator may be configured to compare the measured T-wave alternans with T-wave alternans in a population of infants. The processor may be configured to process the received electrical signals to measure a QT interval of the heart of the infant. The comparator may be configured to compare the measured QT interval with QT intervals in a population of infants. The received electrical signals may include electrocardiogram signals. The system may also include an analog-to-digital converter configured to sample the received electrical signals at a frequency less than or equal to twice a frequency corresponding to alternans to generate sample points.

The processor may be configured to compute an alternating energy at each of the sample points for the series of beats. The processor may include a matrix constructor configured to construct sample point matrices, having rows and columns, from the generated sample points, an adder configured to sum the alternating energy over the entire set of sample points to generate a total alternating energy, and a divider configured to normalize the total alternating energy with respect to an energy of the average waveform. The processor may be configured to create a processed signal having an asymmetric spectrum, and to process the processed signal to generate an indication of alternans in the received electrical signals.

The processor may be configured to create the processed signal as an analytical signal. The processor may be configured to create the processed signal as an analytical signal by generating a frequency domain representation of the received electrical signals, modifying the frequency domain representation to remove components corresponding to negative frequencies, and generating the analytical signal as a time domain representation of the modified frequency domain representation. The input unit may include circuitry configured to receive an electrocardiogram signal. The system may also include an electrode connected to the input unit and configured to produce an electrocardiogram signal. The processor may be configured to sample the electrocardiogram signal at a frequency of once per beat.

By measuring alternans of a heart of the infant, infants at risk for SIDS may be identified. This will help focus preventative measures on the infants most likely to suffer from SIDS, and spare the infants and their families the suffering caused by SIDS.

Other features and advantages will be apparent from the following description, including the drawings, and from the claims.

DETAILED DESCRIPTION

Techniques are provided for using alternans measurements to identify infants at risk for SIDS. Before the techniques are discussed with respect to FIG. 13, more general techniques for detecting and measuring alternans are discussed with respect to FIGS. 1–12B.

Figure 1:
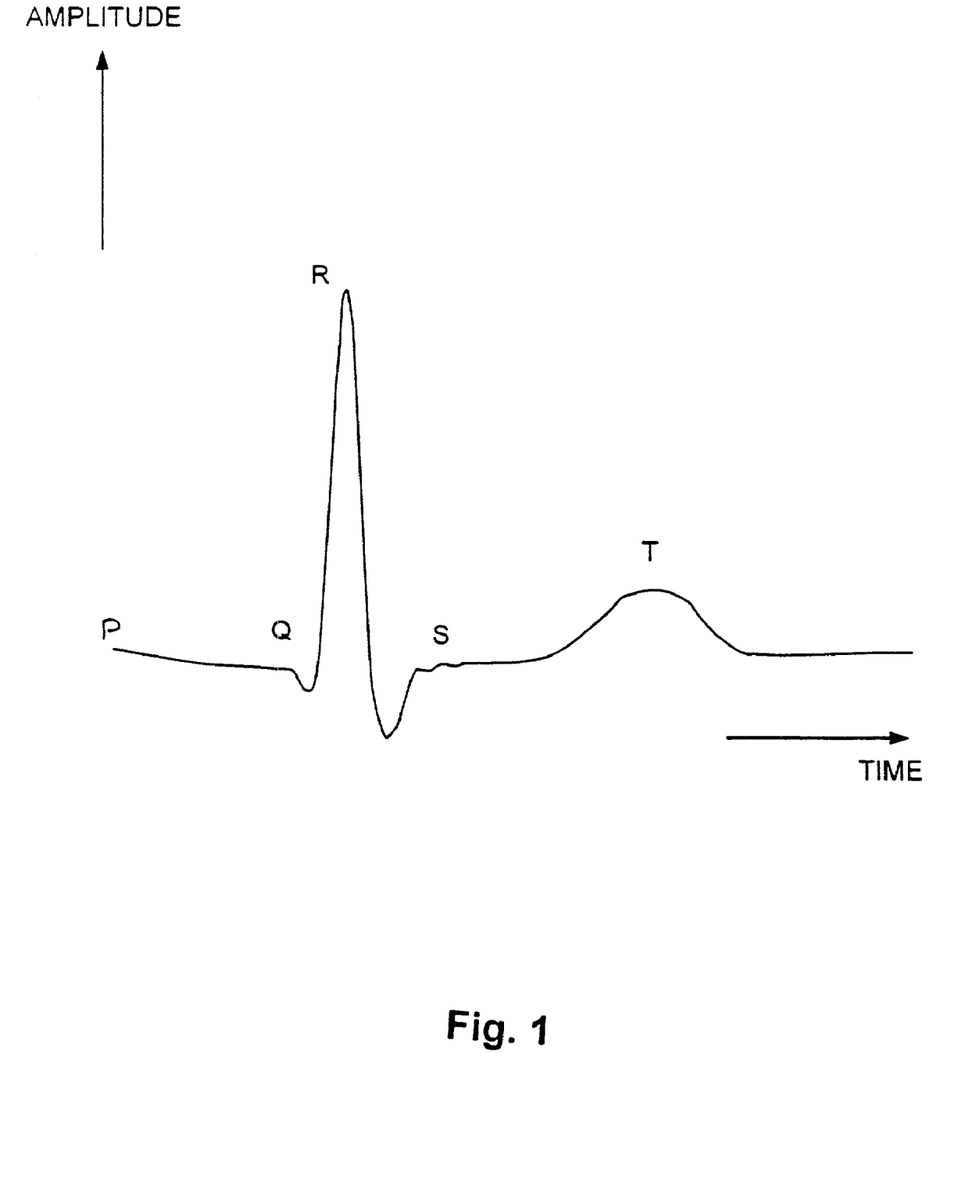
FIG. 1 is a graph of an ECG waveform for a single beat.

Referring to FIG. 1, an ECG waveform for a single beat is typically referred to as a PQRST complex. Briefly, the P wave appears at initiation of the beat and corresponds to activity in the atria, while the QRST complex follows the P wave and corresponds to ventricular activity. The QRS component represents the electrical activation of the ventricles, while the T wave represents their electrical recovery. The ST segment is a relatively quiescent period. The T wave interval of the ECG complex can be monitored to detect alternans. That is, a level of variation in the T waves of alternating beats can indicate the electrical stability of the ventricles—the heart's main pumping chambers.

While an ECG waveform typically has a QRS amplitude measured in millivolts, an alternans pattern of variation with an amplitude on the order of a microvolt may be clinically significant. Accordingly, the alternans pattern may be too small to be detected by visual inspection of the electrocardiogram and often must be detected and quantified electronically. Such electronic detection and quantification of the alternans pattern is further complicated by the presence of noise in the ECG waveforms, as the noise may result in beat-to-beat variations that have a larger magnitude than the alternans pattern of variation.

The noise in an ECG signal can be classified into three categories: baseline noise generated in the electrode, physiologic noise, and external electrical noise. The baseline noise is low frequency noise that appears as an undulating baseline upon which the ECG rides. Baseline noise is attributable to motion and deformation of the electrode, and results from low frequency events such as infant respiration and infant motion. Typically, the frequency content of baseline noise is below 2 Hz.

Physiologic noise results from physiologic processes, such as skeletal muscle activity, that interfere with the ECG signal. The electrical activity of the skeletal muscles creates potentials that are additive with respect to the potentials created by the heart. The frequency content of the skeletal muscle signals is comparable to the frequency content of the QRS complex, and is typically greater than 10 Hz. When measuring T-wave alternans, additional physiologic noise may result from changes in the position of the heart due to respiration or from changes in the projection of the electrical potential from the heart to the skin surface due to thoracic conductivity changes arising from the inflation and deflation of the lungs with respiration.

External electrical noise results, for example, from ambient electromagnetic activity in the room, electrode cable motion, and variations in amplifiers or other components of the ECG circuitry. External electrical noise may be eliminated or reduced through the use of high quality components and through the reduction of ambient electromagnetic activity by, for example, deactivating high power equipment.

The impact of noise upon alternans identification is magnified by the fact that the ABABAB . . . variation in alternating beats occurs at exactly one half the frequency of the beats themselves. By sampling the ECG waveform only once per beat and then trying to determine the alternating beat to beat variation of the samples, the ECG signal cannot be band limited to comply with the Nyquist requirement, as illustrated by FIGS. 2A–4B.

Theoretically, to avoid aliasing when sampling a signal at a given rate, $F_s$, the signal must be band limited to half of the sampling frequency, 0.5 $F_s$, which is referred to as the Nyquist frequency.

Figure 2A:
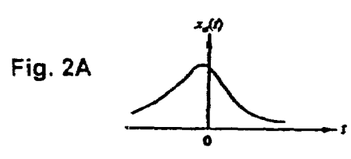
FIGS. 2A and 2B are graphs of, respectively, a band-limited signal and the power spectrum of the signal.
Figure 2B:
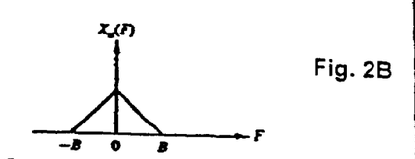

FIGS. 2A and 2B show, respectively, a band-limited analog signal $x_a(t)$ and the power spectrum $X_a(f)$ for that signal. Note that the power spectrum is symmetric about zero.

Figure 3A:
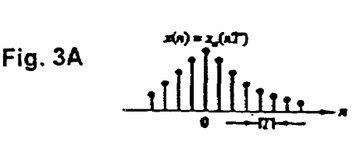
FIGS. 3A and 3B are graphs of, respectively, the band-limited signal of FIG. 2A sampled at a frequency greater than twice the frequency of the highest frequency component of the band-limited signal, and the corresponding power spectrum for the sampled signal.
Figure 3B:
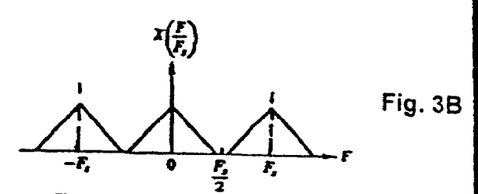

When the analog signal is sampled, the spectrum for the sampled signal is periodic with a period equal to the sampling frequency, $F_s$. FIGS. 3A and 3B show a case in which the sampling frequency is greater than twice the signal bandwidth, 2B. As shown, there is no interference between adjacent spectral periods, and, accordingly, an accurate measurement of signal power at all frequencies of the original analog signal can be made by considering the spectrum for a spectral period.

Figure 4A:
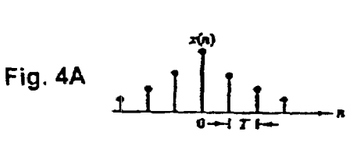
FIGS. 4A and 4B are graphs of, respectively, the band-limited signal of FIG. 2A sampled at a frequency less than twice the frequency of the highest frequency component of the band-limited signal, and the corresponding power spectrum for the sampled signal.
Figure 4B:
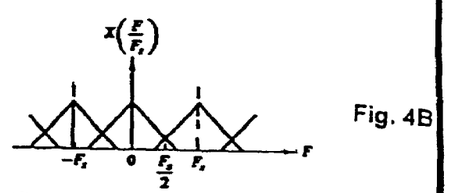

FIGS. 4A and 4B show a case in which the sampling rate is smaller than 2B. As shown, interference between adjacent spectral periods distorts the spectrum for the frequencies of overlap.

As shown in FIGS. 4A and 4B, failure to comply with the Nyquist requirement (i.e., use of a sampling frequency smaller than twice the signal bandwidth) results in underestimation of signal power at all overlapped frequencies including the Nyquist frequency. For alternans detection, the sampling rate is limited to one sample per beat and, since the alternans frequency is at exactly the Nyquist frequency, the signal cannot be band limited to comply with the Nyquist requirement.

Spectral Approach:

One alternans measurement approach that addresses the effects of noise is a spectral approach for measuring T-wave alternans. This approach is described in detail in U.S. Pat. No. 4,802,491, which is incorporated herein by reference. In summary, referring to FIG. 5, a method 500 involves collecting (step 510) using, for example, a high input impedance amplifier and an analog-to-digital converter, and concurrently analyzing 128 beats of a continuous stream of ECG signals using, for example, a programmable processor. The spectral approach uses measurements from time synchronized points of consecutive T waves. A time series is created by measuring, for each of the 128 beats, the T-wave level at a fixed point relating to the QRS complex (step 520). This process is repeated to create a time series for each point in the T-wave. A frequency spectrum is then generated for each time series (step 530), and the spectra are averaged to form a composite T-wave alternans spectrum (step 540). Since the T-waves are sampled once per beat for each time series, the spectral value at the Nyquist frequency, i.e. 0.5 cycle per beat, indicates the level of beat-to-beat alternation in the T-wave waveform.

Figure 5:
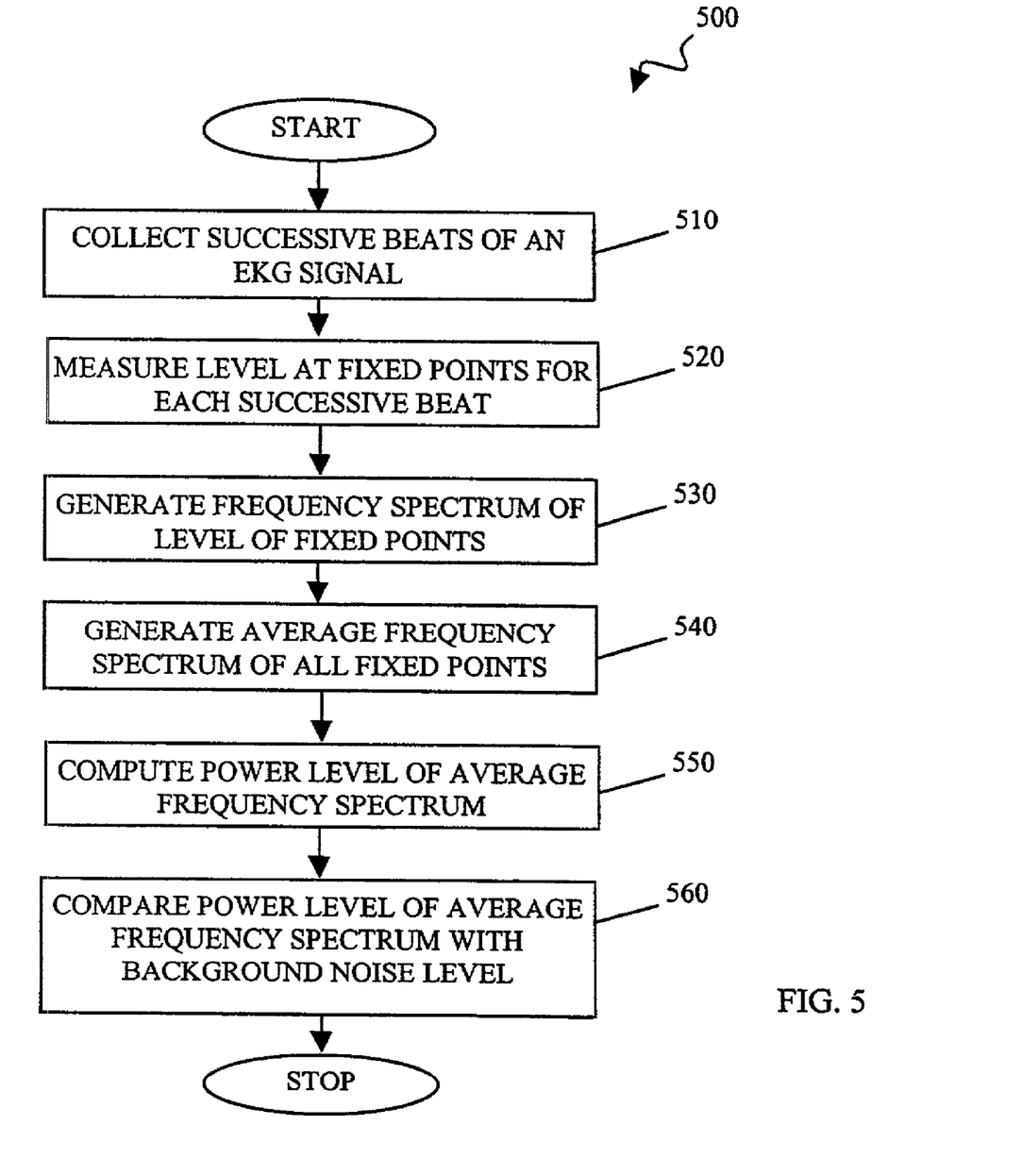
FIG. 5 is a flow chart of a spectral approach for processing ECG signals.

The alternans power is calculated from the composite T-wave alternans spectrum (step 550) and statistically compared to the noise power to discriminate the beat-to-beat T-wave variation due to abnormal electrical activity of the heart from the random variation due to background noise (step 560). The alternans power is calculated by subtracting the mean power in a reference band used to estimate the background noise level (for example, the frequency band of 0.44–0.49 cycle per beat) from the power at the Nyquist frequency (0.50 cycle per beat). Alternans may be considered to be significant if the alternans exceeds noise by a threshold amount. Alternans may be considered to be significant if the alternans is at least three times the standard deviation of the noise in the noise reference band.

The spectral approach for T-wave alternans measurement is accurate in the case of T-wave alternans measured during well controlled motion at ⅓ or ⅔ of the heart rate. This is because two conditions tend to reduce or eliminate the effects of failure to comply with the Nyquist requirement.

First, the noise within the noise band can be considered to be white. Since the spectrum for white noise is flat for all frequencies, there is interference from multiple adjacent spectral cycles. This, in turn, means that interference due to noise is statistically equivalent for all frequencies.

Second, as noted above, the alternans is phased-locked (i.e. the ECG signal is sampled at synchronized points). This means that the signals at the Nyquist frequency interfere with consistent phase, which results in a correct estimation of signal power at this frequency.

Analytical Approach:

Colored noise in the ECG waveform also can mimic the presence of alternans where none exists. For example, if an infant is breathing at one half or one third of the heart rate, the respiration may introduce a harmonic signal having the ABABAB . . . pattern of alternans. Motion that repeats with some periodicity can create electrode noise with a similar pattern. In processing a signal that includes colored noise, errors may result if one assumes that the noise is white, and an analytical approach should be used.

Figure 6A:
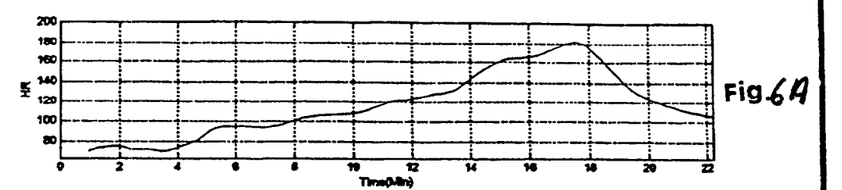
FIG. 6A is a plot of the heart rate of a patient versus time during a motion test.
Figure 6B:
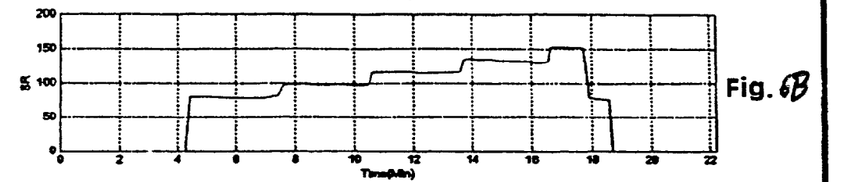
FIG. 6B is plot of the motion rate of the patient versus time.
Figure 6C:
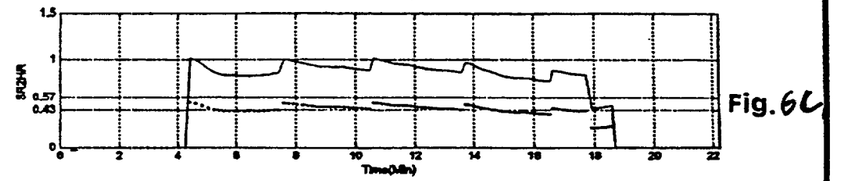
FIG. 6C is a plot of the motion rate divided by the heart rate (solid line) and the first sub-harmonic of the stepping rate divided by the heart rate (dotted line).

For example, artifacts due to infant respiration or due to repetitive infant motion like sucking may cause colored noise to occur in the noise band at the alternans frequency. FIGS. 6A–6C show a typical case in which the rate of a infant's motion is close to the heart rate. FIG. 6A shows the heart rate as a function of time, FIG. 6B shows the motion rate, and FIG. 6C shows the motion rate and its subharmonic, normalized to the heart rate. In this particular case, the motion creates artifacts at frequencies close to half of the heart rate.

In a case such as is illustrated in FIGS. 6A–6C, since the noise within the noise band is colored, interference between components from adjacent spectra of different phase results in underestimation of noise and therefore overestimation of alternans power, which in turn may produce false positive results for T-wave alternans tests.

Figure 7:
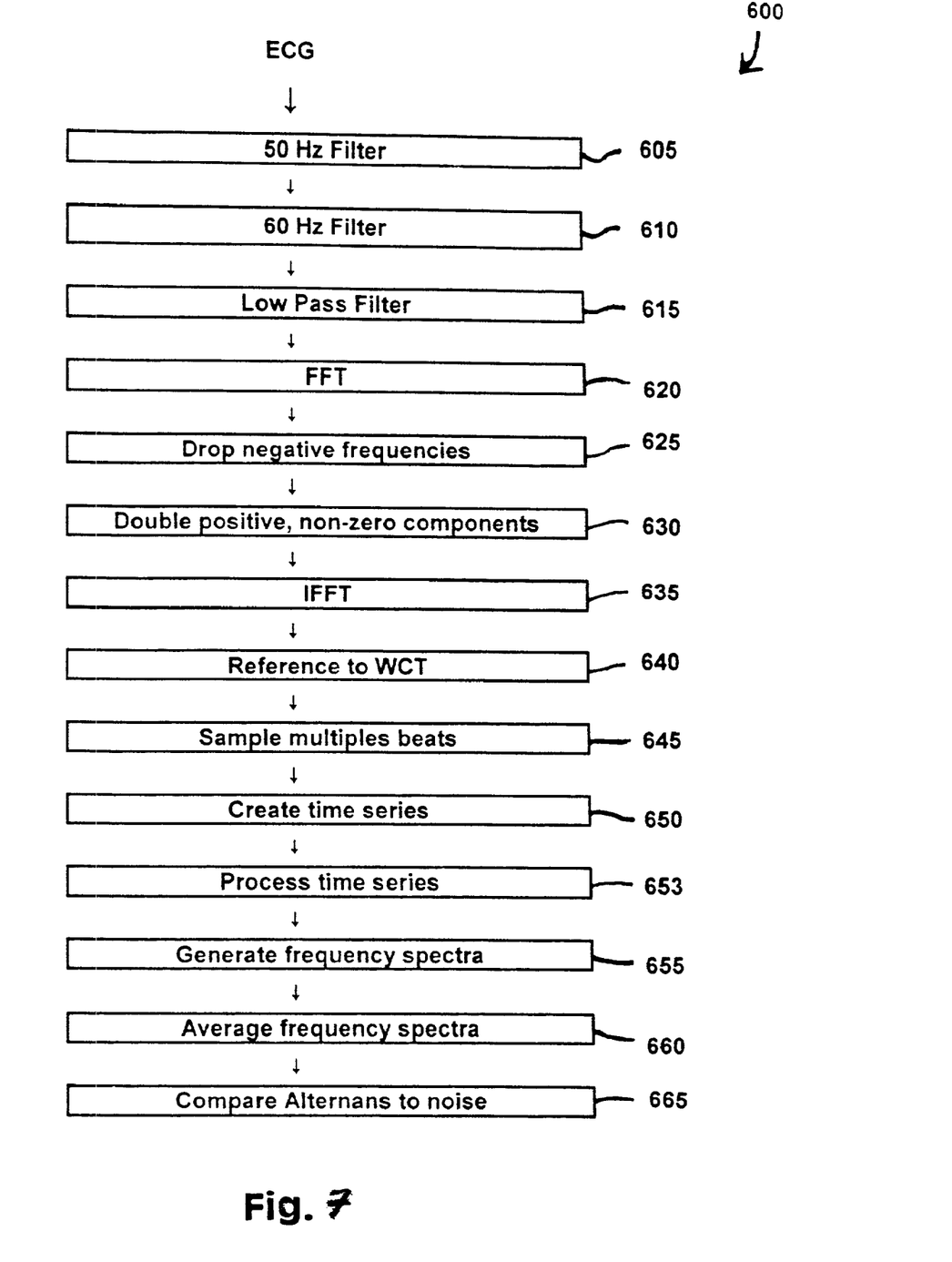
FIG. 7 is a flow chart of an analytical approach for processing ECG signals.

Referring to FIG. 7, problems associated with the presence of colored noise may be avoided through use of an analytical signal technique 600. According to the technique 600, an ECG signal is processed using a 50 Hz filter (step 605) and a 60 Hz filter (step 610). This processing reduces the effects of line voltages used to power the equipment that generates the ECG signal, with 60 Hz being the standard line voltage frequency in the U.S. and 50 Hz being standard in Europe.

Next, an analytical version of the signal is created (steps 615–635). First, the signal is low-pass filtered (step 615). In one implementation, the low pass filter is a $5^{th}$ order Butterworth filter with a zero phase configuration. The filtered signal is then transferred to the frequency domain using a fast Fourier transform (FFT) (step 620).

In the frequency domain, the portions of the frequency spectrum corresponding to negative frequencies are removed (step 625). The technique then compensates for removal of negative frequencies by doubling all positive, non-zero components of the frequency spectrum (step 630). An inverse fast Fourier transform (IFFT) is then performed on the modified frequency spectrum to produce an analytical signal in the time domain (step 635).

Next, the analytical signal is referenced to an analytical version of Wilson's central terminal (step 640). Wilson's central terminal (WCT) is a well-known ECG reference value. The analytical version of WCT is generated from the standard WCT using the procedure set forth in steps 615–635. The analytical signal is referenced to the analytical version of WCT by determining the difference between the two signals.

The referenced analytical signal then is processed similarly to the spectral approach. In particular, the referenced analytical signal is sampled at time synchronized points on the T wave for a collection of 128 beats (step 645), and a time series is created for each point on the collection of T waves (step 650). As in the spectral method, a time series is created by measuring, for each of the 128 beats, the T-wave level at a fixed point relative to the QRS complex. This process is repeated to create a time series for each point in the T wave.

Next, the time series are processed to reduce noise such as that resulting from baseline wander (step 653). In general, this processing uses other signals, including those corresponding to respiration and impedance, to adaptively remove baseline wander. Techniques for processing the time series are described in more detail in U.S. Pat. No. 5,704,365, titled "USING RELATED SIGNALS TO REDUCE ECG NOISE," which is incorporated by reference.

A frequency spectrum is then generated for each time series (step 655), and the spectra are averaged to form a composite T-wave alternans spectrum (step 660). Since the T-waves are sampled once per beat for each time series, the spectral value at the Nyquist frequency, i.e. 0.5 cycle per beat, indicates the level of beat-to-beat alternation in the T-wave waveform.

Finally, the alternans power is statistically compared to the noise power to discriminate the beat-to-beat T-wave variation due to abnormal electrical activity of the heart from the random variation due to background noise (step 665). The alternans power is calculated by subtracting the mean power in a reference band used to estimate the background noise level from the power at the Nyquist frequency (0.50 cycle per beat). In one implementation, the reference band includes frequencies from 0.43 to 0.49 and 0.51 to 0.56 cycles per beat. In the same implementation, alternans is considered to be significant if it is at least three times the standard deviation of the noise in the noise reference band.

In general, the technique 600 reduces or eliminates the effects of aliasing. The amount of aliasing depends on the infant's heart rate and reduces as the heart rate increases. For heart rates of primary interest, such as 95 to 175 beats per minute, the sampling frequency is approximately 2.5 Hz. In the spectral method, this would have meant that any signal component of frequency content over 1.25 Hz would be a source of aliasing.

Since aliasing is primarily due to the interference between the frequency components at the positive part of the spectrum and those at the negative part of the spectrum from an adjacent period of the spectrum, creation of an analytical signal serves to avoid aliasing. In particular, creation of the analytical signal removes the interfering negative frequency components while scaling the signal to preserve the total signal energy.

An analytical signal is a complex signal. See Proakis J G, Manolakis D G, *Digital Signal Processing*, Prentice Hall, Upper Saddle River, N.J., 1996, pp. 738–742, which is incorporated by reference. The real part of the complex signal, y, is the original signal, x, and the imaginary part is the Hilbert transform, H(x), of the original signal:

$$y = x + jH(x),$$

where H(x) is the Hilbert Transform of x with the following transfer function.

$$H(\omega) = \begin{cases} -j & \text{for } 0 < \omega \leq +\pi \\ +j & \text{for } -\pi < \omega \leq 0 \end{cases}$$

The Hilbert Transform returns a complex sequence. This sequence is a version of the original real sequence with a 90° phase shift. It has the same amplitude and frequency content as the original real data and includes phase information that depends on the phase of the original data.

The overall transform has the following real transfer function:

$$H_a(\omega) = \begin{cases} 0 & \text{for } -\pi < \leq 0 \\ 1 & \text{for } \omega = 0 \\ 2 & \text{for } 0 < \omega \leq +\pi \end{cases}$$

The analytic signal is characterized as having an asymmetric spectrum with components of negative frequency having been removed. A variety of time domain and frequency domain processing methods and filters that can be used to implement or approximate the analytic signal approach. These methods affect certain frequencies $\omega_n$ of the input signal differently for the positive frequency $+|\omega_n|$ and the corresponding negative frequency $-|\omega_n|$. The result is a signal having an asymmetric spectrum. Examples of suitable processing methods and filters include, but are not limited to, spectral windowing functions and time domain functions which convolve the input signal with a signal whose spectrum is asymmetric. There are a number of techniques that may be used to create suitable functions. These techniques include, but are not limited to, Chebyshev approximation, FIR or IIR filter design, windowing techniques, recursive design techniques, and inverse Z-transform techniques.

Figure 8A:
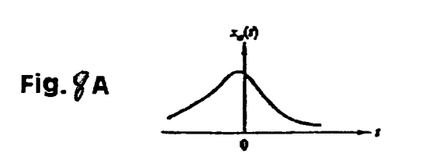
FIGS. 8A and 8B are graphs of, respectively, a band-limited signal and the power spectrum of the signal.
Figure 8B:
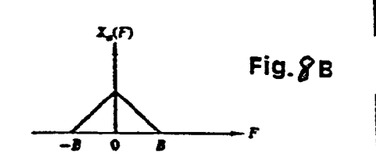
Figure 9:
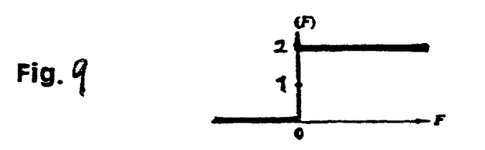
FIG. 9 is a graph of the transfer function of a filter used to generate an analytical signal from a band-limited signal.
Figure 10:
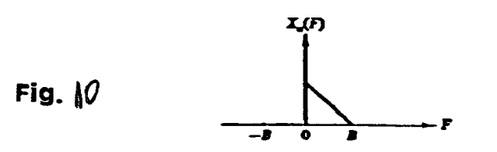
FIG. 10 is a graph of a power spectrum of the analytical signal.
Figure 11A:
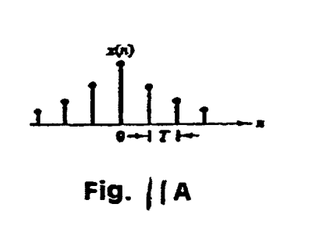
FIGS. 11A and 11B are graphs of, respectively, the analytical signal sampled at a frequency less than twice the frequency of the highest frequency component of the band-limited signal, and the corresponding power spectrum.
Figure 11B:
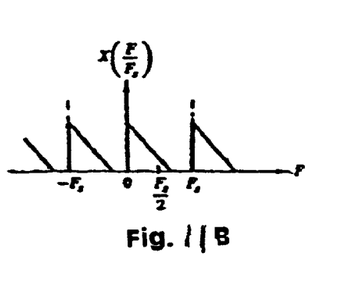

The band-limited signal shown in FIG. 8A has the power spectrum shown in FIG. 8B. When the filter shown in FIG. 9 is applied to the signal of FIG. 8A, an analytical signal having the power spectrum shown in FIG. 10 is created. That signal then may be sampled at a frequency less than twice the bandwidth, as shown in FIG. 11A. For an electrocardiogram signal, by down sampling the signal at T-wave locations, the digital spectrum is still a periodic spectrum with a period of 1/sampling interval, i.e., the heart rate. As shown in FIG. 11B, interference between the positive and negative frequencies is eliminated since the negative part of the spectrum is removed.

Figure 12A:
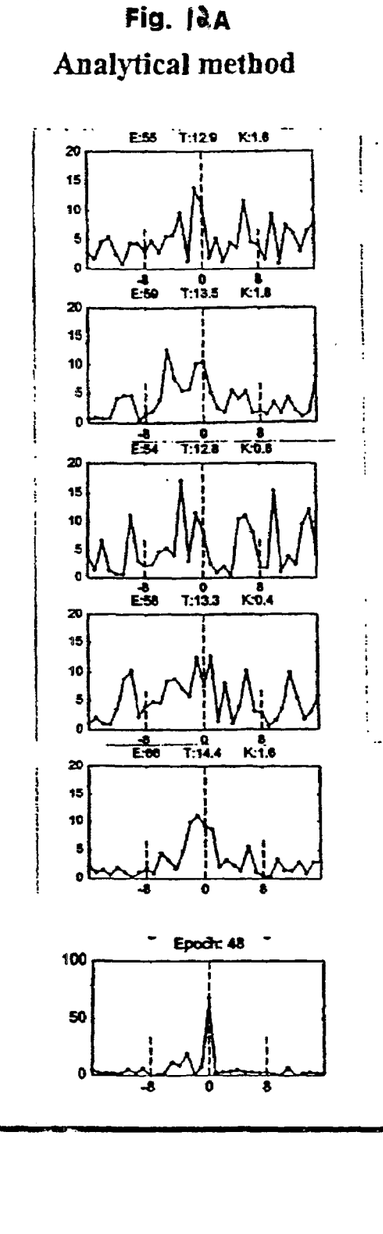
FIGS. 12A and 12B are graphs of power spectra generated using, respectively, an analytical signal approach and the spectral method.
Figure 12B:
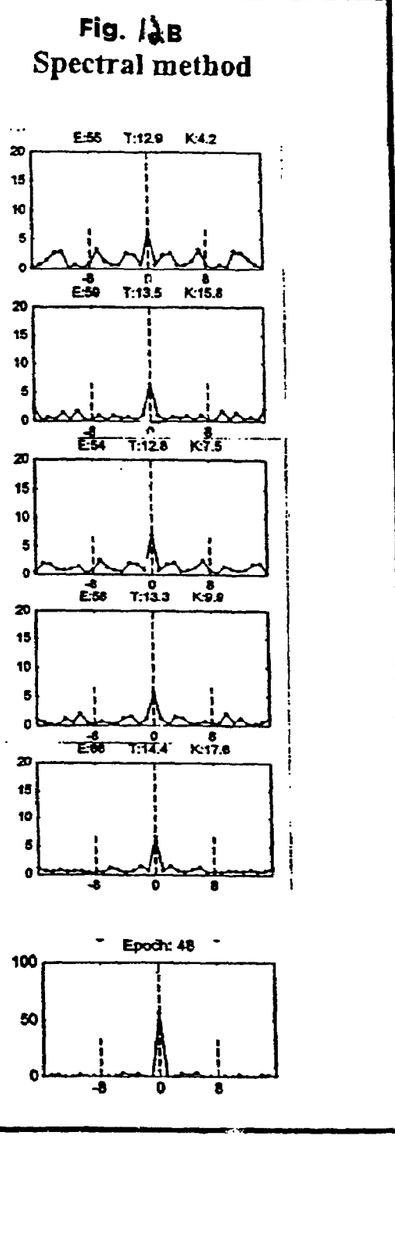

This approach allows an accurate measurement of T-wave alternans even when there is colored noise at or close to alternans frequency, such as may occur during infant motion. FIGS. 12A and 12B illustrate a comparison between the analytical approach and the spectral approach. It is evident that the presence of colored noise within the noise band results in an overestimation of alternans power and underestimation of noise power in the spectral approach. By contrast, the analytical approach provides an accurate estimation of both the alternans and the noise within the noise band.

Figure 13:
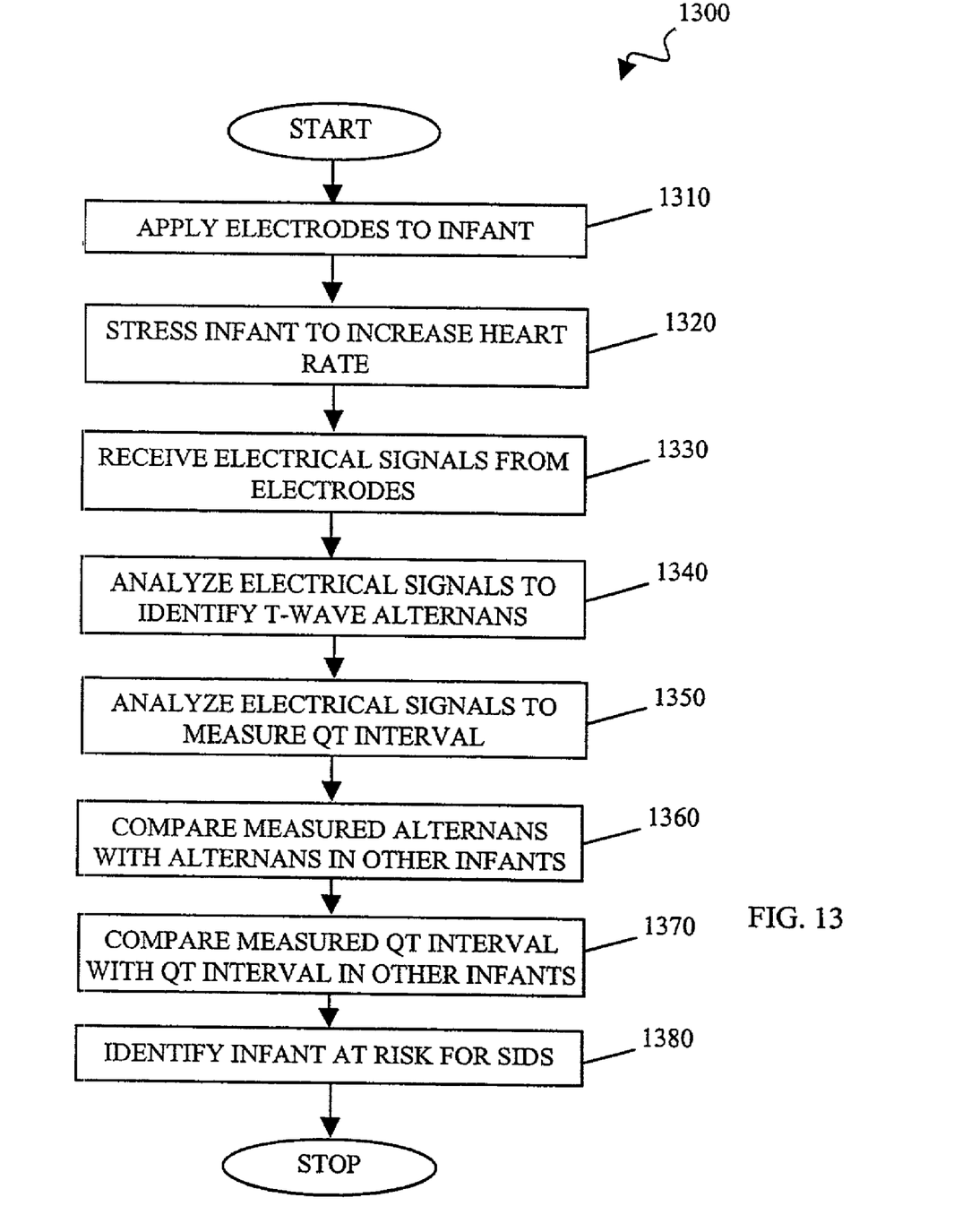
FIG. 13 is a flow chart of a method for identifying infants at risk for SIDS.

Referring to FIG. 13, in a procedure 1300 for identifying infants at risk for SIDS, a physician or other operator first places ECG electrodes on the infant (step 1310). For example, seven MICRO-V ALTERNANS SENSORS (Cambridge Heart, Bedford, Mass.) and seven standard electrodes may be placed in the standard 12-lead configuration, as well as 4 Frank vector positions, on the infant. After the electrodes have been applied, the operator then "stresses" the infant to increase the infant's heart rate (step 1320). Although the infant may not be able to perform common stress tests like a treadmill stress test, other stress tests such as changing the infant's position, tickling or pinching the infant, shouting or otherwise startling the infant, administering drugs, removing a parent from the infant's line of sight, feeding the infant, or waiting for a bowel movement by the infant may be used to increase the heart rate of the infant.

Electrical signals from the electrodes are received during the stress test using, for example, the HEARTWAVE SYSTEM (Cambridge Heart, Bedford, Mass.) or another ECG system capable of processing the data (step 1330). The received electrical signals are then electronically analyzed to identify T-wave alternans in the ECG of the infant using, for example, a programmable processor (step 1340). Analysis may include performing either the analytical approach or the spectral approach discussed above.

Next, the QT interval in the infant's ECG is measured (step 1350). T-wave alternans measurement from the patient infant is compared with T-wave alternans in one or more infant populations (step 1360) and the QT interval measurement from the patient infant with QT intervals in one or more infant populations (step 1370) using, for example, a programmable processor acting as a comparator. By performing one or both of these comparisons, infants at risk for SIDS may be identified (step 1380) so that preventative measures reducing the likelihood of death of the infant can be taken.

In one implementation, in order to identify infants at risk for SIDS, the measured alternans of the heart is analyzed and classified. The measured alternans may be accessed and automatically analyzed to produce one or more interpretation parameters. The interpretation parameters may be used to generate interpretation results related to the alternans data to classify the alternans data, and the interpretation results may be made accessible for examination.

The measured alternans may include data related to a reference signal associated with a factor that affects the quality of the alternans measures or the generation of the alternans. For example, with respect to the quality of the alternans measures, the reference signal may include a signal that masks or mimics the presence of alternans. The reference signal also may include a measure of noise that exists in the data. Signals that may affect the generation of alternans include, for example, a measure of the patient's heart rate or respiratory activity.

The interpretation parameters may include a measure of a highest heart rate in the data or a highest heart rate at which sustained alternans is definitely not present. Other examples include a measure of a heart rate above which sustained alternans exists and below which sustained alternans does not exist, or an indication of the existence or non-existence of sustained alternans.

Analyzing the alternans data may include automatically evaluating a measure of alternans that is indicative of the presence of sustained alternans. For example, the measure of alternans may include a measure of a voltage or of an area associated with the alternans. Likewise, the measure of the alternans may include a measure of a power spectrum of the alternans or a dynamically estimated magnitude of the alternans, obtained, for example, by complex demodulation of the electrocardiogram. A measure of noise associated with the alternans, e.g., a measure of a standard deviation of the noise, also may be indicative of sustained alternans. Other examples include measures of a temporal duration of the alternans, of gaps in the alternans, or of a measure of the alternans based upon evaluation of time reversed alternans data.

Analyzing the alternans data may include, for example, automatically using a first search to search the alternans data for sustained alternans. After using the first search, a different search also may be used to search the alternans data for sustained alternans. The different search may be used, for example, when the first search does not find sustained alternans in the alternans data or when a determination is made that the findings of the first search are suspect as a result of a poor quality of the alternans data.

Analyzing the alternans data also may include evaluating the data provided by an individual electrocardiogram lead or evaluating a combination of adjacent precordial electrocardiogram leads.

The interpretation results that are generated to classify the measured alternans may include the interpretation parameter and/or a clinical interpretation regarding the existence of sustained alternans in the alternans data. The clinical interpretation may, for example, positively indicate the existence of sustained alternans, negatively indicate the existence of sustained alternans, or indicate that the existence of sustained alternans is indeterminate.

Using the interpretation parameter to calculate the interpretation results may include using the interpretation parameter to traverse a decision tree to produce the interpretation results based on the alternans data. Another example includes comparing the interpretation parameter to a heart rate threshold to produce the interpretation results based on the alternans data.

The interpretation results may be made accessible for examination by, for example, graphically displaying the alternans measure, the reference signal, and the interpretation results. The interpretation results also may be made accessible by storing the alternans measure, the reference signal, and/or the interpretation results in a human or machine readable format. In any event, the alternans measure and the reference signal may be displayed using a common time axis and the interpretation results may be graphically associated to an associated feature of the alternans measure and/or the reference signal. A message describing the interpretation results also may be included.

The alternans trend report is evaluated by a trained physician, who assigns a clinical interpretation of "positive," "negative" or "indeterminate" to the alternans result. The alternans trend data may be difficult to interpret, especially when the alternans exists in the presence of noise or abnormal ECG beats. Ultimately, the physician must exercise subjective judgment based on his or her own experience and training to determine whether the alternans is significant and sustained, and to estimate the values of Onset HR (the heart rate at the onset of sustained alternans), Max Neg. HR (the highest heart rate at which alternans is definitively not present), and other parameters. The accuracy and reliability of the interpretation of the trend data therefore varies from physician to physician as a function of experience and training. This inter-reader variability diminishes the predictive value of the alternans test and is avoided by the automatic interpretation.

Further information about the analysis and classification of measured alternans can be found at U.S. application Ser. No. 09/785,558, filed Feb. 20, 2001, and entitled "AUTO- MATED INTERPRETATION OF T-WAVE ALTERNANS RESULTS," the contents of which are incorporated herein by reference.

A process embodying these techniques may be performed by a programmable processor executing a program of instructions to perform desired functions by operating on input data and generating appropriate output data. The techniques may be implemented in one or more computer programs that are executable on a programmable system including at least one programmable processor coupled to receive data and instructions from, and to transmit data and instructions to, a data storage system, at least one input device configured to receive the ECG signals, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially-designed ASICs (application-specific integrated circuits).

Other implementations are within the scope of the following claims.

What is claimed is:

1. A method for identifying infants at risk for SIDS, comprising:
    applying electrodes to an infant;
    receiving electrical signals from the electrodes;
    analyzing the received electrical signals to measure alternans of a heart of the infant; and
    identifying whether the infant is at risk for SIDS using the measured alternans,
    wherein alternans comprise a beat-to-beat ABABAB change in an amplitude of an ECG waveform of the infant.

2. The method of claim 1 wherein:
    analyzing the received electrical signals comprises measuring T-wave alternans; and
    identifying whether the infant is at risk for SIDS comprises comparing the measured T-wave alternans with T-wave alternans in a population of infants.

3. The method of claim 1 wherein identifying whether the infant is at risk for SIDS comprises analyzing and classifying the measured alternans of the heart.

4. The method of claim 1 further comprising elevating a heart rate of the infant.

5. The method of claim 4 wherein elevating the heart rate of the infant includes stressing the infant.

6. The method of claim 1 further comprising analyzing the received electrical signals to measure a QT interval of the heart of the infant.

7. The method of claim 6 further comprising comparing the measured QT interval with QT intervals in a population of infants.

8. The method of claim 1 wherein the received electrical signals comprise electrocardiogram signals.

9. The method of claim 1 wherein analyzing the received electrical signals includes sampling the received electrical signals at a frequency less than or equal to twice a frequency corresponding to alternans.

10. The method of claim 1 wherein analyzing the received electrical signals includes using a spectral approach to measure alternans.

11. The method of claim 1 wherein analyzing the received electrical signals includes using an analytical approach to measure alternans.

12. The method of claim 11 wherein using the analytical approach includes:
    processing the received electrical signals to create a processed signal having an asymmetric spectrum; and
    processing the processed signal to measure alternans in the received electrical signals.

13. The method of claim 12 wherein processing the received electrical signals to create a processed signal comprises creating the processed signal as an analytical signal.

14. The method of claim 13 wherein creating the processed signal as an analytical signal comprises generating a frequency domain representation of the received electrical signals, modifying the frequency domain representation to remove components corresponding to negative frequencies, and generating the analytical signal as a time domain representation of the modified frequency domain representation.

15. The method of claim 12 wherein processing the processed signal includes processing samples of the processed signal spaced by intervals greater than or equal to half of a period of alternans.

16. The method of claim 12 wherein processing the received electrical signals comprises creating an approximation of an analytical signal version of the received electrical signals.

17. The method of claim 16 wherein processing the processed signal includes sampling the processed signal at a frequency less than or equal to twice a frequency corresponding to alternans.

18. A method for identifying infants at risk for SIDS, comprising:
    applying electrodes to an infant;
    receiving electrical signals from the electrodes;
    analyzing the received electrical signals to measure alternans of a heart of the infant; and
    comparing the measured alternans with alternans in a population of infants to identify whether the infant is at risk for SIDS,
    wherein alternans comprise a beat-to-beat ABABAB change in an amplitude of an ECG waveform of the infant.

19. The method of claim 18 wherein:
    analyzing the received electrical signals comprises measuring T-wave alternans; and identifying whether the infant is at risk for SIDS comprises comparing the measured T-wave alternans with T-wave alternans in a population of infants.

20. The method of claim 18 further comprising elevating a heart rate of the infant.

21. The method of claim 20 wherein elevating the heart rate of the infant includes stressing the infant.

22. The method of claim 18 further comprising analyzing the received electrical signals to measure a QT interval of the heart of the infant.

23. The method of claim 22 further comprising comparing the measured QT interval with QT intervals in a population of infants.

24. The method of claim 18 wherein the received electrical signals comprise electrocardiogram signals.

25. The method of claim 18 wherein analyzing the received electrical signals includes sampling the received electrical signals at a frequency less than or equal to twice a frequency corresponding to alternans.

26. The method of claim 18 wherein analyzing the received electrical signals includes using a spectral approach to measure alternans.

27. The method of claim 26 wherein using the spectral approach to measure alternans comprises:
digitizing the waveform of the received electrical signals at a plurality of sample points for each cycle; and
constructing two-dimensional sample point matrices, having rows and columns, from the digitized waveform.

28. The method of claim 27 wherein using the spectral approach to measure alternans further comprises analyzing variability in each column of the sample point matrices to form an index correlating with stability of the received electrical signals.

29. The method of claim 27 wherein using the spectral approach to measure alternans further comprises:
computing alternating energy at each of the sample points; and
summing the alternating energy over all of the sample points to generate a total alternating energy.

30. The method of claim 18 wherein analyzing the received electrical signals includes using an analytical approach to measure alternans.

31. The method of claim 30 wherein using the analytical approach includes:
processing the received electrical signals to create a processed signal having an asymmetric spectrum; and
processing the processed signal to measure alternans in the received electrical signals.

32. The method of claim 31 wherein processing the received electrical signals to create a processed signal comprises creating the processed signal as an analytical signal.

33. The method of claim 32 wherein creating the processed signal as an analytical signal comprises generating a frequency domain representation of the received electrical signals, modifying the frequency domain representation to remove components corresponding to negative frequencies, and generating the analytical signal as a time domain representation of the modified frequency domain representation.

34. The method of claim 31 wherein processing the processed signal includes processing samples of the processed signal spaced by intervals greater than or equal to half of a period of alternans.

35. The method of claim 31 wherein processing the received electrical signals comprises creating an approximation of an analytical signal version of the received electrical signals.

36. The method of claim 35 wherein processing the processed signal includes sampling the processed signal at a frequency less than or equal to twice a frequency corresponding to alternans.

* * * * *